United States Patent
Hagg et al.

(10) Patent No.: US 9,949,782 B2
(45) Date of Patent: Apr. 24, 2018

(54) METHOD FOR THE CONTROL OF A MEDICAL DEVICE AS A FUNCTION OF NEUTRAL ELECTRODE IMPEDANCE

(75) Inventors: Martin Hagg, Wannweil (DE); Juergen Beller, Gomaringen (DE); Peter Selig, Hechingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 934 days.

(21) Appl. No.: 13/495,129

(22) Filed: Jun. 13, 2012

(65) Prior Publication Data
US 2012/0323236 A1    Dec. 20, 2012

(30) Foreign Application Priority Data
Jun. 20, 2011   (EP) .................... 11170577

(51) Int. Cl.
*A61B 18/12* (2006.01)
*A61B 18/16* (2006.01)
*A61B 18/00* (2006.01)

(52) U.S. Cl.
CPC ...... *A61B 18/1206* (2013.01); *A61B 18/1233* (2013.01); *A61B 18/16* (2013.01); *A61B 2018/00642* (2013.01); *A61B 2018/00672* (2013.01); *A61B 2018/00678* (2013.01); *A61B 2018/00708* (2013.01); *A61B 2018/00875* (2013.01); *A61B 2018/00898* (2013.01)

(58) Field of Classification Search
CPC . A61B 18/1233; A61B 18/1206; A61B 18/16; A61B 2018/00642; A61B 2018/00875; A61B 2018/00898
See application file for complete search history.

(56) References Cited

U.S. PATENT DOCUMENTS

| 4,416,276 A | 11/1983 | Newton et al. |
| 4,416,277 A * | 11/1983 | Newton ............. A61B 18/1233 128/908 |
| 2011/0202055 A1* | 8/2011 | Selig ............................. 606/41 |

FOREIGN PATENT DOCUMENTS

| CN | 200942123 | 9/2007 |
| CN | 201088626 | 7/2008 |
| CN | 201356649 | 12/2009 |
| CN | 101945618 | 1/2011 |
| DE | 3239640 A1 | 5/1983 |
| DE | 68924918 T2 | 6/1996 |
| JP | S58-103445 A | 6/1983 |
| WO | WO 2009109197 A1 | 9/2009 |
| WO | WO 2010049145 A1 * | 5/2010 ............... A61B 5/01 |

* cited by examiner

*Primary Examiner* — Joseph Dietrich
(74) *Attorney, Agent, or Firm* — Blank Rome LLP

(57) ABSTRACT

The method disclosed herein permits the operator of an electrosurgical device to move a safety switch-off threshold for a contact resistance at a neutral electrode from a first value to a second and slightly higher value. This way, for patients with a relatively high resistance yielding a somewhat elevated contact resistance despite correct attachment of the neutral electrode, uninterrupted operation of the device is achievable.

5 Claims, 3 Drawing Sheets

METHOD FOR THE CONTROL OF A MEDICAL DEVICE AS A FUNCTION OF NEUTRAL ELECTRODE IMPEDANCE

RELATED APPLICATION

This application claims priority to European patent application EP 11 170 577.8, filed on Jun. 20, 2011, which is hereby incorporated by reference in its entirety.

TECHNICAL FIELD

Embodiments of the invention relate to a method for the control of a medical device as a function of the impedance measured at the neutral electrode, and to a corresponding electrosurgical device.

BACKGROUND

With electrosurgical devices, in particular those used in monopolar high frequency (HF) surgery, an electromedical device is used to supply power to an instrument to be used by the surgeon for desired operations such as for example, tissue fusions, coagulations, ablations or the like. If the instrument is monopolar, it is supplied with HF power via a line. A neutral electrode, to be attached to the patient over a large area, is used to close the electrical circuit. A current path is therefore provided that extends from the active instrument via the body of the patient back to the electromedical device. The current should pass through the neutral electrode with as little damage to the tissue as possible. Any rises in temperature at the neutral electrode should remain small to avoid thermal tissue effects or even damage at this point. It is therefore desirable to limit the current density. For this reason, the neutral electrode has a large contact area. The greater the contact area of the neutral electrode, the lower the resultant current density and the heating it induces.

If electrodes have a large surface area, they must contact the patient as fully as possible to prevent local concentrations of current. The electrode is therefore generally split into two sections that both contact the skin of the patient. The impedance to be measured between the two sections, or the contact resistance, is compared to a limit value. If the impedance exceeds the limit value, then activation of the HF surgical device is prevented.

The limit value for the tissue impedance must be set to a relatively low value to effectively detect an incorrect (i.e., incomplete) contact of the neutral electrode. However, in patients with dry skin or a thick layer of subcutaneous adipose tissue, this will lead to the impedance threshold being exceeded and the deactivation of the HF surgical device even though the neutral electrode is correctly attached to the patient. This leads to difficulties in the operating theatre. The usual approaches of cleaning or wetting the skin, using larger neutral electrodes or searching for more suitable points at which to attach the electrodes so that the value falls below the limit value results at least in a disruption of the usual surgical routine and also to an additional time expenditure. An increase in the threshold value is not a real alternative because of the associated danger of failing to recognize an incorrect attachment of the electrode to patients with a low skin resistance. This could result in damage to the skin at the point of attachment.

SUMMARY

Accordingly, it is an object herein to provide a method for controlling an electromedical device that, on one hand, affords high patient safety and, on the other hand, ensures that the operating procedure is free of major disruptions wherever possible.

With the concepts in accordance with the present disclosure, the correct attachment of the neutral electrode is determined by an impedance measurement between at least two sections of the neutral electrode. The measured impedance characterizes the contact resistance from the neutral electrode to the patient. If the value of the measured impedance is below a first limit value, then the operation of the device is enabled without restriction. If, however, the electrical impedance between the two sections is above this first limit value, then operation of the electromedical device is initially disabled. An appropriate warning signal, which may be a visual and/or audible signal, is generated for this purpose; the warning signal may be for example, an audible signal together with an image or text display on a monitor. After noting the warning signal, the operator can check the correct full-area contact of the neutral electrode and then enter an appropriate user command that confirms the correct attachment of the neutral electrode. The user command can be a keystroke or other inputs.

The input of the user command allows the disablement to be ended, thus enabling operation of the electrosurgical device, although the impedance at the neutral electrode has exceeded the first limit value. To end the disabled operation, the limit value can be reset at least temporarily to a higher value.

Damage to the skin of the patient is not expected, following a manual check of the attachment of the electrode and subsequent ending of the disabled operation by the user input, since the increased impedance is not due to incorrect attachment of the neutral electrode but instead to other factors such as e.g., a thick layer of subcutaneous tissue. The embodiments of the invention thus provide a way of minimizing the interruption of the surgical operation despite the monitoring of the attachment of the neutral electrode by comparing the impedance with a threshold value.

In a preferred embodiment, the disabled operation can only be ended upon a first limit value being exceeded if the measured impedance is lower than a second and higher limit value. If the second and higher limit value is also exceeded, then it is not possible for the operator to end the disabled operation. This response can be achieved for example if the first threshold value is replaced at least temporarily by the second, higher threshold value.

As an alternative, the ending of the disabled operation when the second limit value is exceeded may only be allowed in exceptional cases such as for example, after repeated and, if necessary, cleared warnings. Moreover, according to another embodiment described herein, the device can be operated only for a short time (i.e., the operating time is restricted to one or more short intervals). Additionally or alternatively, the device, in particular its generator, can only be operated in this case with a reduced output.

In the preferred embodiment, the control device of the electromedical device differentiates between three conditions: A) a condition with impedance below the first limit value, where the electromedical device can be operated without restriction; B) an impedance which is between the first and second limit values, where the electromedical device can only be operated in a restricted manner after manual ending of the initially automatic disabling of the device; and C) if the impedance is above the second limit value, then further operation of the medical device is preferably completely disabled.

The aforementioned functions permit the commencement of the surgical procedure, even on patients with critical tissue impedance values, almost without time delay and additional expenditure. Nevertheless, the safety of the application for patients with low tissue impedance values is not diminished and an automatic monitoring of the quality of the attachment of the neutral electrode is still assured. The impedance can be repeatedly or continuously monitored during operation of the electrosurgical device. The repeated check of the impedance can take place e.g., periodically or from time to time. For example, if the impedance is continuously or repeatedly monitored when the first limit value is exceeded, and following manual ending of the disablement of operation, it is possible to check if the impedance is gradually falling. This is possible if the temperature of the neutral electrode increases to the surface temperature of the body and also if there is transpiration underneath the electrode. Electrolytes can be emitted by the skin, increasing the conductivity and reducing the impedance.

If a fall in the impedance value below the first limit value is detected, then this can to a certain degree, be reactivated and thereafter be regarded as a limit value. If the first limit value is exceeded again, then a warning can again be emitted and/or the operation of the electromedical device disabled again. The first limit value can be changed slightly (e.g., additionally lowered) to bring about a hysteresis for switching back and forth between the first and the second limit values. It is also possible for the device to request attachment of a larger neutral electrode if the first limit value is exceeded again or if the second limit value is exceeded after manual enabling. This too can serve to avoid time delays in the operating theatre.

If a first limit value is exceeded, but a second limit value is not, then it is possible for the device to be operated at a reduced output rather than be completely disabled. It is therefore possible to continue to operate surgical instruments that are operated at low output even though a higher impedance value is measured at the neutral electrode. For example, in this case with an impedance below the first limit value, the device can permit operation with an unrestricted high output. Furthermore, if the impedance is above the first limit value, but below the second limit value, then the device can permit operation with a reduced output. If the second limit value is exceeded, then according to an embodiment, the device will not permit any further operation. Optionally, in the second case, if the impedance is between the first and the second limit values, manual enabling can be carried out, after which operation with unrestricted output is possible.

BRIEF DESCRIPTION OF THE DRAWINGS

Numerous variations of the aforementioned methods are possible. Hereinafter, exemplary embodiments of the invention are explained in greater detail with reference to drawings, in which.

DETAILED DESCRIPTION

Figure 1:
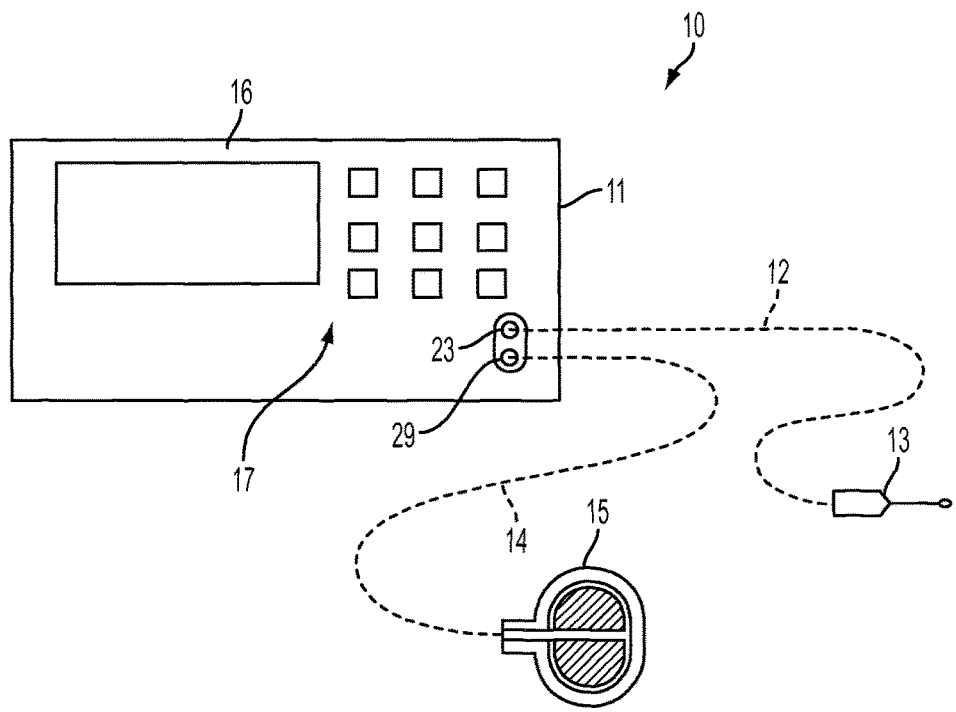
FIG. 1 illustrates an electrosurgical device with connected instrument and neutral electrode.

An electrosurgical device 10 is shown in FIG. 1, with which is associated an electromedical device 11 that supplies power to a surgical instrument 13 via line 12 and is connected to a neutral electrode 15 via line 14. While the surgical instrument 13 in the hand of the surgeon is used to carry out surgical interventions in a patient, the neutral electrode 15 is intended to close the current circuit via the patient. It is attached to the patient over a large area at a suitable point such as for example, the thigh.

The device 11 used to supply power to the instrument 13 has at least one display device 16 (for example, a monitor) and operating elements 17 (for example, keys, operating knobs or the like). Further or different operating elements and display devices can be provided.

Figure 2:
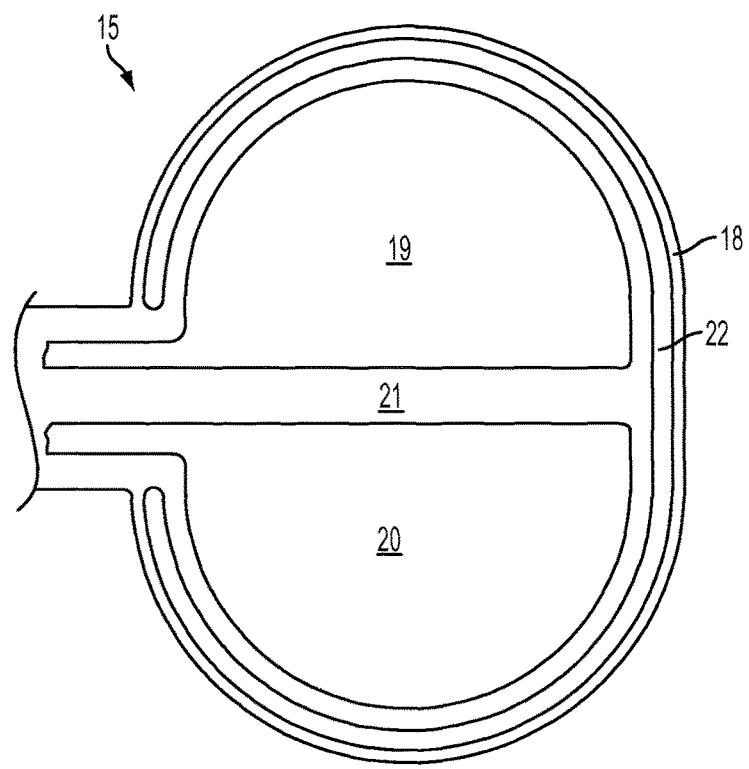
FIG. 2 illustrates the neutral electrode according to FIG. 1.

The neutral electrode 15 is shown separately in FIG. 2. It comprises a non-electrically conducting carrier 18, on which is disposed at least two metallic sections 19, 20 of large area. These sections 19,20 can be designed as e.g., thin metal foils or as metallic coatings. The sections 19, 20 are at a distance 21 from one another and are thus electrically insulated from one another. A further metallic section 22 arranged on the carrier 18 can envelop the two sections 19, 20 and thus provide a uniform electrical potential along the edge of the carrier 18.

The sections 19, 20 are connected to the device 11 via different strands of line 14. Optionally (as an alternative to or additionally), the section 22 can be connected to the device 11 via a strand of line 14.

Figure 3:
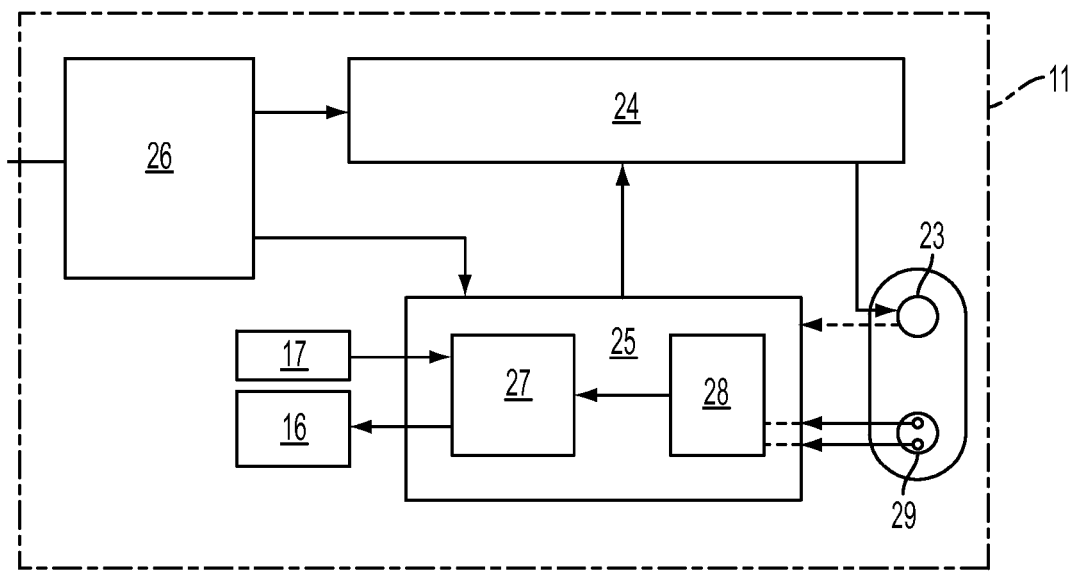
FIG. 3 illustrates the electrosurgical device in the form of a block diagram.

FIG. 3 illustrates the fundamental structure of the device 11. A socket 23 for connection of line 12 and hence of the instrument 13 is connected to an electrical generator 24 (for example, an HF generator). The socket 23 can be of single-pole or multi-pole design. In addition to a contact transferring the HF power of the generator 24, it can have one or more contacts for further strands of line 12 by which control signals, for example, can be sent to a control device 25 of the device 11. The corresponding line connection is shown in FIG. 3 as a dashed line.

The central control device 25 controls the generator 24. Control device 25 is provided with an operating voltage by a power supply unit 26. The control device 25 is connected to the operating elements 17 and to the display device 16. It has a central processing module 27 comprising one or more computers (for example, microcomputers) to provide the functions described below.

The control device 25 further comprises a module 28 for the determination of the impedance between the sections 19, 20 of the neutral electrode 15 when the latter is attached to a patient. To do so, the module 28 is connected to two contacts of a connection (for example, in the form of a socket 29) to which line 14 must be attached. The two contacts are assigned to different strands of line 14, one of which leads to section 19 and the other to section 20 of the neutral electrode 15. The two contacts are connected to module 28, as can be seen from FIG. 3.

The module 28 records the impedance or the apparent impedance between the two sections 19, 20 e.g., continuously or intermittently. For this operation, the module 28 can apply, continuously or repeatedly, a low voltage to the sections 19, 20 and record the current that results. Alternatively, a specified current can be applied and the voltage recorded. The current and/or the voltage used for measurement purposes in each case can be a DC voltage, an AC voltage, or an alternating current or s direct current of suitable waveform and frequency. The impedance or the apparent impedance between the sections 19, 20 is preferably evaluated. However, it is also possible to record only the real component or only the imaginary component of the impedance and to use this component in the procedure described below as an indicator of the quality of the neutral electrode attachment.

The module 28 can also be designed to determine the impedance between one of the sections 19, 20 and section 22. The neutral electrode can also be divided into several sections, between which the module 28 determines the impedance. Impedance measurement may be continuous or intermittent in each embodiment. With impedance measurement between several pairs of conductor surfaces, this may be performed in parallel or serially. The procedure described herein can be applied to every pair of conductor surfaces.

The module 28 can be a part of the control device or it can be a separate assembly. Irrespective of this, the module 28 delivers continuously or repeatedly, or just once if desired, a signal to the processing module 27, where this signal characterizes the recorded impedance or variables derived therefrom. The processing module 27 then determines whether the recorded impedance is below a first, limit value G1 and above or below a second limit value G2. The first limit value G1 is e.g., 120 ohms. The second limit value G2 is e.g., 140 ohms. It should be appreciated that the limit values G1, G2 can, however, be assigned different values.

Figure 4:
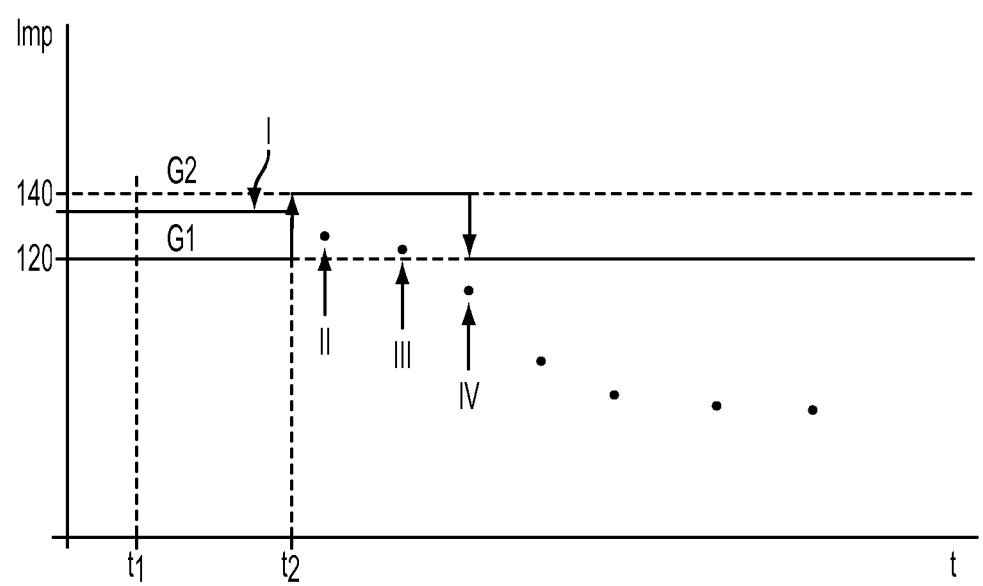
FIG. 4 illustrates the time curve of tissue impedance measurements and associated fixed limit values by way of example.

The mode of operation of the processing module 27 is illustrated diagrammatically in FIG. 4. If the impedance Imp determined by the module 28 is below limit value G1, then the control device 25 enables the operation of the generator 24 without any restriction. It is assumed in this scenario that the neutral electrode 15 is correctly attached. For example, requirement signals received via the socket 23 can cause the control device 25 to activate the generator 24 so that HF power is available at the instrument 13. A surgeon can then perform the desired surgical interventions without delay.

FIG. 4 illustrates a situation in which the impedance Imp in accordance with the curve I is above the first limit value G1, but below the second limit value G2. The reasons for this may vary. For example, it is possible that the neutral electrode 15 has not been correctly attached. It is also possible that the impedance Imp is elevated because of dry skin or other patient attributes. The device 11 commences an impedance measurement at time t1 and establishes that the impedance Imp is between the first and second limit values G1, G2. The device 11 then disables normal operation, so that the generator 24 can no longer be operated. A signal is sent via the display device 16 requesting that the operator check for a correct attachment of the neutral electrode 15.

Once this has happened, the operator can confirm via one of the operating elements 17, for example at time t2, that the electrode is correctly attached and thus enables operation of the generator. The second limit value G2 is now the upper limit for the impedance Imp. In so far as and for as long as this is not exceeded, operation is enabled. If the second limit value G2 has been exceeded, however, then operation of the generator 24 would once again be disabled (and cannot be overridden).

In the example according to FIG. 4, operation of the device 11 is now possible since the impedance Imp is between limits G1 and G2 and the correct attachment of the neutral electrode to the patient has been checked and verified. It is now assumed that the surgeon actuates the instrument 13. Therefore, or also irrespectively thereof, the impedance Imp may fall over time, for example due to moistening of the skin underneath the neutral electrode 15. It can be optionally provided that the control device 25 determines the impedance continuously or, as shown, at discrete time intervals. While corresponding measured values II and III are still above the first limit value G1, a further measured value IV is already below the first limit value G1. This can be attributed to the development of perspiration underneath the neutral electrode 15. In a preferred embodiment, the processing module 27 now restores the first limit value G1 as the active limit value for operation of the device 11. If this value is exceeded again, then the device will be disabled again at least for the time being, as described above.

Figure 5:
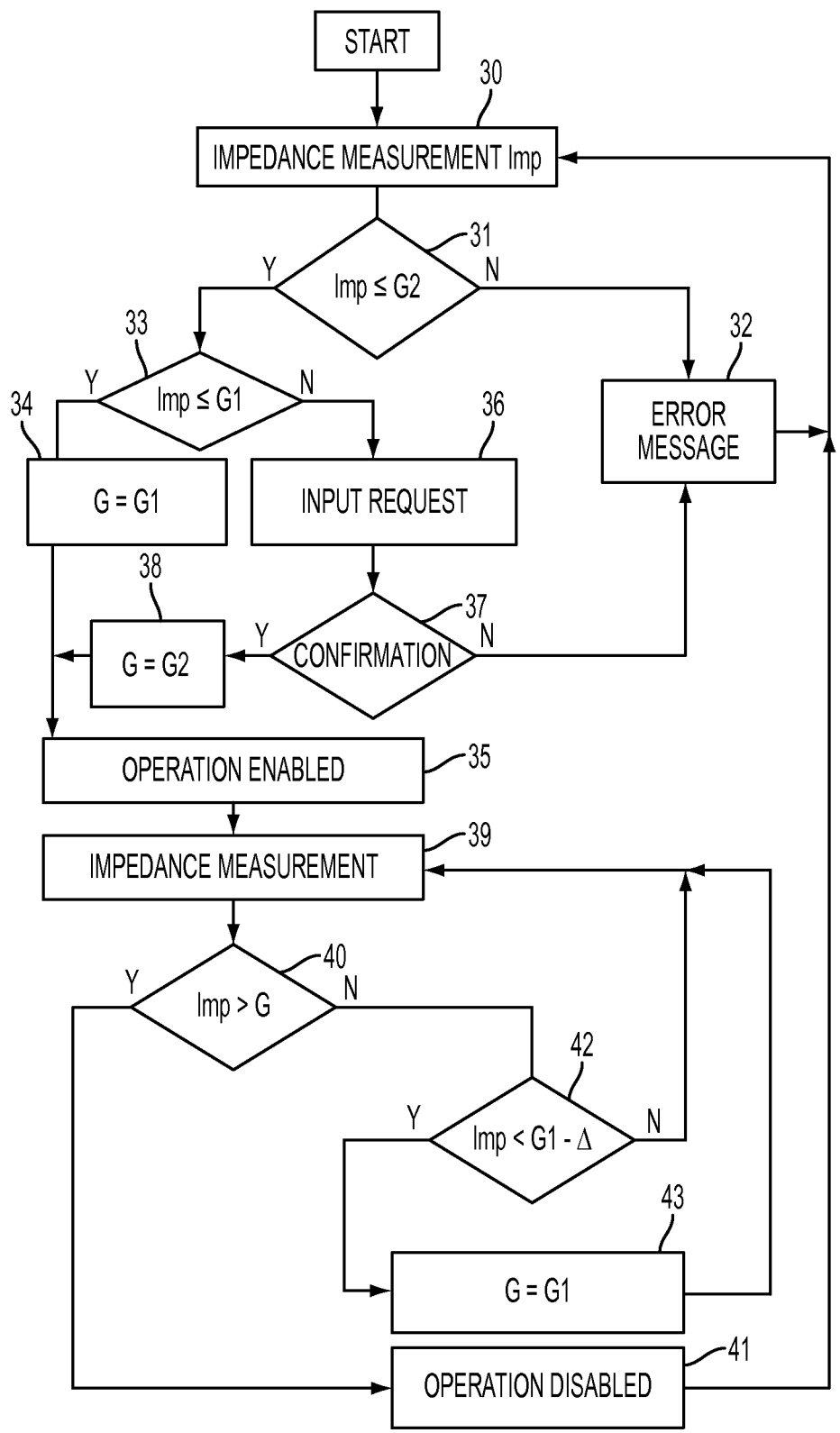
FIG. 5 illustrates a flow diagram for an example implementation of the method in accordance with the present disclosure.

The method according to invention can be carried out on the basis of the flow diagram shown in FIG. 5. After commencement of the processing procedure, the impedance Imp between sections 19 and 20 is measured in block 30. The impedance Imp is first compared with the second limit value G2 (e.g., 140 ohms) in block 31. If the impedance exceeds the second limit value G2, then the system continues at block 32 in which operation of the generator 24 is prevented and an error message appears on the monitor of the display device 16. The process then repeats the measurement of the impedance Imp (at block 30).

If, however, it is determined at block 31 that the impedance Imp is less than (or the same as) the second limit value G2, then it is checked at block 33 whether the impedance Imp is below (or the same as) the first limit value G1. If this is the case, then a limit value variable G=G1 is set at block 34 and the operation of the generator 24 is enabled at block 35. If, however, it is determined that the impedance Imp is greater than G1, i.e. it is between G1 and G2, then the method continues at block 36 where the user is requested for confirmation that the neutral electrode 15 is correctly attached. If the user confirms the correct attachment of the neutral electrode at block 37, then the limit value variable G=G2 is set at block 38 and operation is enabled at block 35. If there is no confirmation, or not within a specified time interval, then the method continues at block 32, or alternatively to block 30, whereby the impedance is measured again with (block 32) or without emission of an error message.

If operation has been enabled at block 35, the impedance is measured again at block 39. At block 40 is determined whether the measured impedance Imp is greater than the limit value variable G (set above). If it is determined that the measured impedance Imp is greater than the limit value variable G, then operation is disabled at block 41 and the process reverts to block 32 or block 30. If it is determined that the measured impedance Imp is not greater than the limit value variable G, then the process continues at block 42 where it is determined whether the impedance Imp is lower than the first limit value G1 minus a hysteresis value Δ. If it is determined that the impedance Imp is not lower than G1 minus Δ, then the process switches to block 39. If, however, it is determined that the impedance Imp is less than G1−Δ, then the limit value G is set back to the first limit value G1 at block 43 and the process reverts to block 39.

The flow diagram described above shows the use of two different limit values G1, G2. If the first limit value G1 for the impedance Imp is exceeded, then the user can raise arbitrarily the safety switch-off threshold of the device 11 to the second limit value G2 via an appropriate input. It is not, however, possible to exceed the second limit value G2 for safety reasons.

The method in accordance with the disclosed embodiments of the invention permits the operator of an electrosurgical device 11 to move its safety switch-off threshold for the contact resistance at the neutral electrode 15 from a first low value G1 to a second and somewhat higher value G2 so that, for patients with a relatively high resistance where the contact resistance is somewhat high despite correct attachment of the neutral electrode 15, operation of the device 11 is uninterrupted and the instrument 13 is enabled.

What is claimed is:

1. An electrosurgical device comprising:
   an electrical generator to supply power to an electrosurgical instrument,
   a connection for a neutral electrode for attachment to a patient, the neutral electrode having at least two sections that are electrically insulated from one another, and
   a control device having a control module to record the electrical impedance between the two sections and which is connected to the electrical generator, said control module configured to:
     enable without restriction operation of the generator if the measured impedance is below a first limit value,
     disable operation of the generator if the measured impedance exceeds the first limit value,
     generate a warning signal if the measured impedance is above the first limit value and below a second limit value that is greater than the first limit value,
     end the disablement upon input of an appropriate user command if the measured impedance is above the first limit value and below the second limit value, and
     disable operation of the generator such that it cannot be overridden when the impedance exceeds the second limit value,
   wherein the first limit value and second limit value are fixed.

2. The device of claim 1, wherein the generator is a high frequency (HF) generator.

3. The device of claim 1, wherein the control device repeatedly monitors the impedance during operation of the generator.

4. The device of claim 1, wherein after the first limit value has been exceeded and a subsequent manual enabling of the operation of the generator has occurred, the control device continuously monitors the impedance to determine whether the first limit value has been exceeded again and, in such an event, emits a warning and/or disables operation of the generator once again.

5. The device of claim 4, wherein re-enabling operation of the generator can occur abased on receiving an input signal to end the disablement.

* * * * *